United States Patent
Ahn et al.

(10) Patent No.: US 10,539,526 B2
(45) Date of Patent: Jan. 21, 2020

(54) MICRO SENSOR

(71) Applicant: POINT ENGINEERING CO., LTD., Asan (KR)

(72) Inventors: Bum Mo Ahn, Suwon (KR); Seung Ho Park, Hwaseong (KR); Sung Hyun Byun, Asan (KR)

(73) Assignee: POINT ENGINEERING CO., LTD., Asan (KR)

( * ) Notice: Subject to any disclaimer, the term of this patent is extended or adjusted under 35 U.S.C. 154(b) by 24 days.

(21) Appl. No.: 15/674,463

(22) Filed: Aug. 10, 2017

(65) Prior Publication Data

US 2018/0045664 A1 Feb. 15, 2018

(30) Foreign Application Priority Data

Aug. 12, 2016 (KR) .................. 10-2016-0103055

(51) Int. Cl.
*G01N 27/12* (2006.01)

(52) U.S. Cl.
CPC ......... *G01N 27/128* (2013.01); *G01N 27/123* (2013.01)

(58) Field of Classification Search
CPC ...................... G01N 27/128; G01N 27/123
See application file for complete search history.

(56) References Cited

U.S. PATENT DOCUMENTS

| | | | |
|---|---|---|---|
| 5,167,158 A * | 12/1992 | Kamachi | G01L 9/0055 338/3 |
| 2001/0034502 A1* | 10/2001 | Moberg | A61M 5/1456 604/154 |
| 2007/0164417 A1* | 7/2007 | Todd | G01J 5/02 257/685 |
| 2012/0318058 A1* | 12/2012 | Kimura | G01F 1/6842 73/204.23 |
| 2015/0075258 A1* | 3/2015 | Paik | G01N 27/041 73/31.06 |

FOREIGN PATENT DOCUMENTS

| | | |
|---|---|---|
| CN | 105492898 A | 4/2016 |
| CN | 105784786 A | 7/2016 |
| CN | 106158743 A | 11/2016 |
| JP | 2010-164411 A | 7/2010 |
| JP | 5009867 B2 | 8/2012 |
| KR | 10-2009-0064693 A | 6/2009 |
| KR | 10-2015-0031709 A | 3/2015 |
| KR | 10-2015-0112224 A | 10/2015 |
| KR | 10-2016-0035820 A | 4/2016 |

* cited by examiner

*Primary Examiner* — Farhana A Hoque

(57) ABSTRACT

Disclosed is a micro sensor. Particularly, disclosed is a micro sensor capable of changing a resistance value of a resistance unit connected to a sensor electrode depending on a sensing material, the resistance unit having at least two resistors.

20 Claims, 9 Drawing Sheets

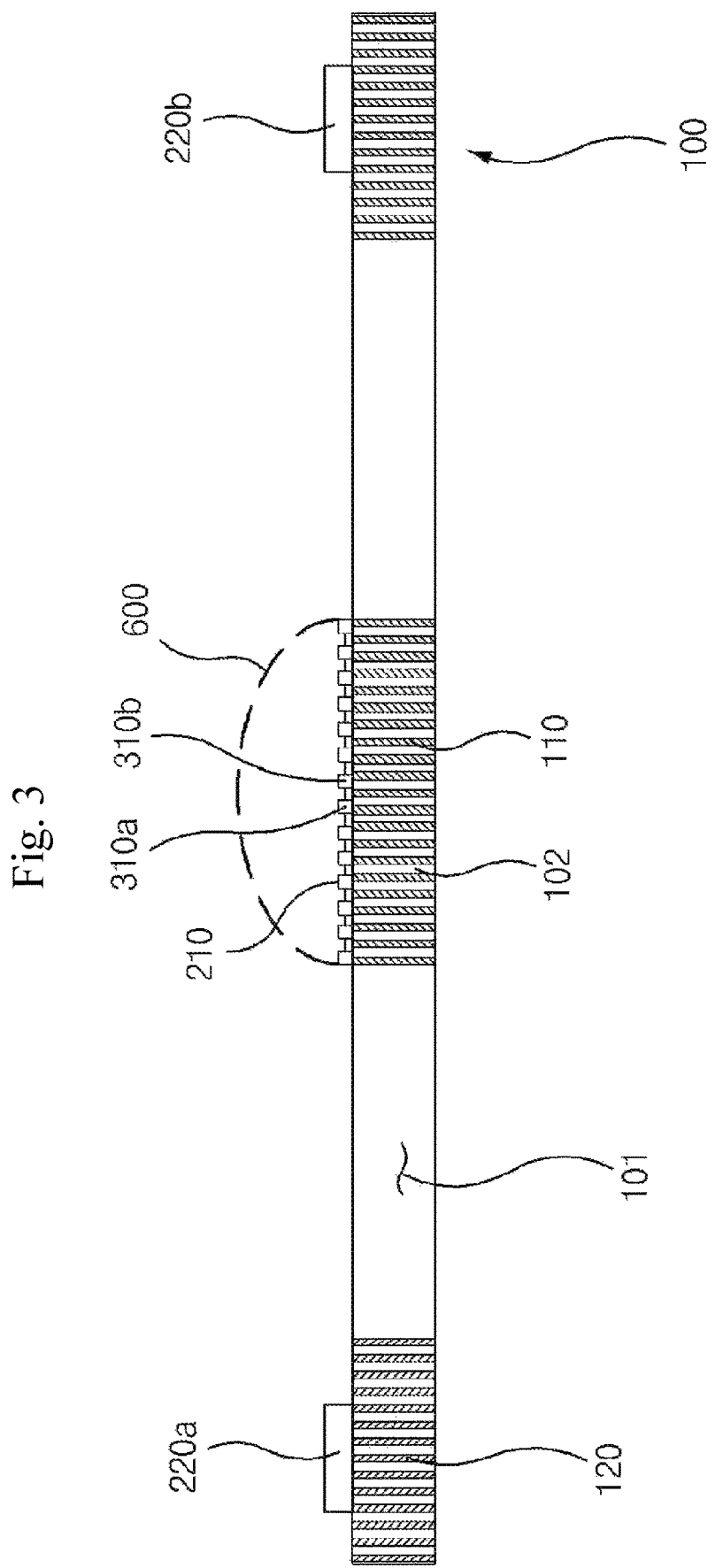

MICRO SENSOR

CROSS REFERENCE TO RELATED APPLICATION

The present application claims priority to Korean Patent Application No. 10-2016-0103055, filed Aug. 12, 2016, the entire contents of which is incorporated herein for all purposes by this reference.

BACKGROUND OF THE INVENTION

Field of the Invention

The present invention generally relates to a micro sensor. More particularly, the present invention relates to a micro sensor including a resistance unit connected to a sensor electrode, the resistance unit having at least two resistors.

Description of the Related Art

Recently, as concern about the environment is gradually increasing, there is a need for development of a micro sensor being capable of acquiring accurate and various pieces of information in a short period of time. Especially, for comfort of residential space, management of harmful industrial environment, management of foods and food production processes, etc., efforts have progressed in terms of realizing miniaturization, high-precision, and cost reduction of a micro multi-array sensor, such as a gas sensor, for easily measuring the relevant gas concentration.

Gas sensors are gradually evolving from conventional sintered ceramic or thick film structures into micro-electro-mechanical system (MEMS) gas sensors by applying semi-conductor process technologies.

In terms of a measurement method, the most widely used method of a gas sensor today is measuring changes in electrical characteristics when the gas is adsorbed onto a sensing material of the sensor. Generally, metal oxides such as $SnO_2$ are used as a sensing material, and the change in the electrical conductivity thereof depending on the concentration of the target gas is measured. This measurement method is relatively simple. Here, the change in the measurement value is more significant when the metal oxide sensing material is operated at the high temperature. Therefore, precise temperature control is essential for fast and precise measurement of the gas concentration. Also, when measuring, the gas concentration is measured after resetting the sensing material to its initial state through high temperature heating, thereby forcibly removing gas species or moisture already adsorbed onto the sensing material.

Generally, in order for the gas sensor to be applied to IT devices by packaging the gas sensor, an analog output (resistance output) mode is required to be changed into a digital output (voltage output) mode. To this end, resistance, which is similar to or equal to a resistance value, is required to be applied to a sensing material of the gas sensor, and thus the resistance of an end of the sensing material is required to be changed into a voltage. However, the sensing material is problematic in that sensing efficiency is reduced because a resistance value of the base material changes according to a temperature, and thus an initial resistance value is irregular.

To solve this problem, Korean Patent Application Publication No. 10-2015-0031709 and Korean Patent Application Publication No. 10-2015-0112224 disclose a gas sensor package provided with an output changing section such as an NTC (negative temperature coefficient thermistor) or a fixed resistor.

In the meantime, the resistance differs depending on a sensing material. Therefore, the resistance value of the output changing section differs depending on a sensing material. However, a conventional sensor is problematic in that the sensor package cannot be used in common due to a fixed resistor provided in the output changing section.

Also, the conventional sensor is problematic in that the volume of the conventional sensor is large due to the NTC or the resistance element applied to the output changing section.

The foregoing is intended merely to aid in the understanding of the background of the present invention, and is not intended to mean that the present invention falls within the purview of the related art that is already known to those skilled in the art.

DOCUMENTS OF RELATED ART (Patent Document 1) Korean Patent Application Publication No. 10-2015-0031709.
(Patent Document 2) Korean Patent Application Publication No. 10-2015-0112224.
(Patent Document 3) Korean Patent Application Publication No. 10-2009-0064693.

SUMMARY OF THE INVENTION

Accordingly, the present invention has been made keeping in mind the above problems occurring in the related art, and an object of the present invention is to provide a micro sensor being capable of applying various sensing materials to the sensor.

In order to accomplish the above object, the present invention provides a micro sensor including: a substrate; a sensor electrode provided on the substrate; and a resistance unit provided on the substrate, the resistance unit being electrically connected to the sensor electrode, wherein the resistance unit includes at least two resistors.

At least two of the resistors may have different resistance values.

The resistance unit may include a first, a second, and a third resistance pad and a first resistor, the first resistance pad may be connected to the sensor electrode, at least one of the second resistance pad and the third resistance pad may include both a pad electrode portion of which at least a part is connected to the first resistor and a bonding portion connected to the pad electrode portion, the bonding portion being provided on the substrate at a portion other than the first resistor, and the pad electrode portion may be in contact with the first resistor by intersecting with the first resistor, whereby the pad electrode portion is in contact with opposite ends of the first resistor.

The first resistor may be provided on an upper portion of the pad electrode portion.

The first resistor may be formed of at least one of NiCr, AgMn, CuNi, Ta, TaSi, and C.

The resistance unit may include a first, a second, a third, and a fourth resistance pad and a first and a second resistor, the first resistance pad may be connected to the sensor electrode, a first end of the first resistor may be connected to the first resistance pad, a second end of the first resistor may be connected to the second resistance pad, a first end of the second resistor may be connected to the third resistance pad, and a second end of the second resistor may be connected to the fourth resistance pad.

The resistance unit may include a first, a second, and a third resistance pad and a first and a second resistor, the first resistance pad may be connected to a first sensor electrode pad of the sensor electrode, the second resistance pad or the third resistance pad may be connected to a second sensor electrode pad of the sensor electrode, a first end of the first resistor may be connected to the first resistance pad, a second end of the first resistor may be connected to the second resistance pad, a first end of the second resistor may be connected to the first resistance pad, and a second end of the second resistor may be connected to the third resistance pad.

The resistance unit may include a first and a second resistance pad and a first and a second resistor, the first resistance pad may be connected to the sensor electrode, a first end of the first resistor may be connected to the first resistance pad, a second end of the first resistor may be connected to the second resistance pad, a first end of the second resistor may be connected to the first resistance pad, and a second end of the second resistor may be connected to the second resistance pad.

The resistance unit may include a first, a second, and a third resistance pad and a first and a second resistor, the first resistance pad may be connected to the sensor electrode, a first end of the first resistor may be connected to the first resistance pad, a second end of the first resistor may be connected to the second resistance pad, a first end of the second resistor may be connected to the first resistance pad, and a second end of the second resistor may be connected to the third resistance pad.

The resistance unit may include a first, a second, and a third resistance pad and a first, a second, and a third resistor, the first resistance pad may be connected to the sensor electrode, first ends of the first and the second resistors may be connected to the first resistance pad, second ends of the first and the second resistors may be connected to the second resistance pad, a first end of the third resistor may be connected to the first resistance pad, and a second end of the third resistor may be connected to the third resistance pad.

The resistance unit may include a first, a second, and a third resistance pad and a first and a second resistor, the first resistance pad may be connected to the sensor electrode, a first end of the first resistor may be connected to the first resistance pad, a second end of the first resistor may be connected to the second resistance pad, a first end of the second resistor may be connected to the second resistance pad, and a second end of the second resistor may be connected to the third resistance pad.

The micro sensor may include a heater electrode provided on the substrate, wherein the heater electrode may include a heating wire closer to a sensor wire than to a sensor electrode pad of the sensor electrode.

The substrate may be provided with an air gap surrounding the heating wire.

The substrate may be an anodized film obtained by anodizing a metallic base material and removing the base material.

At least one of the resistors may be a sheet resistor.

At least one of the resistors may be provided in a pattern shape.

At least two of the resistors may be connected to each other in parallel.

At least two of the resistors may be connected to each other in series.

According to the micro sensor of the present invention as described above, effects as follows may be obtained.

The resistance value can be adjusted by selectively connecting the resistors to the sensor electrode, whereby various sensing materials can be applied to the sensor.

The substrate is provided with the air gap surrounding the heating wire of the heater electrode, thereby enhancing insulation performance. Also, the air gap is provided between the heating wire and the resistance unit. Thus, a portion heated by the heating wire is prevented from being influenced by the heat generated from the resistance unit.

The resistance unit includes the first, the second, and the third resistance pads and the first resistor. The first resistance pad is connected to the sensor electrode. At least one of the second resistance pad and the third resistance pad includes both the pad electrode portion of which at least a part is connected to the first resistor, and the boding portion connected to the pad electrode portion, the bonding portion being provided at a portion other than the first resistor. The pad electrode portion is in contact with the first resistor by intersecting with the first resistor, whereby the pad electrode portion is in contact with opposite ends of the first resistor. Accordingly, various values of resistance can be designed by using only one resistor, whereby the structure can be simple.

The first resistor is placed at the upper portion of the pad electrode portion, thereby enhancing stability.

The substrate is the anodized film obtained by anodizing the metallic base material and removing the base material, thereby enhancing insulation effect.

At least one of the resistors is the sheet resistor, or is formed in the pattern shape, thereby minimizing the volume of the resistance unit.

BRIEF DESCRIPTION OF THE DRAWINGS

The above and other objects, features and other advantages of the present invention will be more clearly understood from the following detailed description when taken in conjunction with the accompanying drawings, in which:

FIG. 3 is a cross-sectional view of B-B portion of FIG. 1;

DETAILED DESCRIPTION OF THE INVENTION

Figure 1:
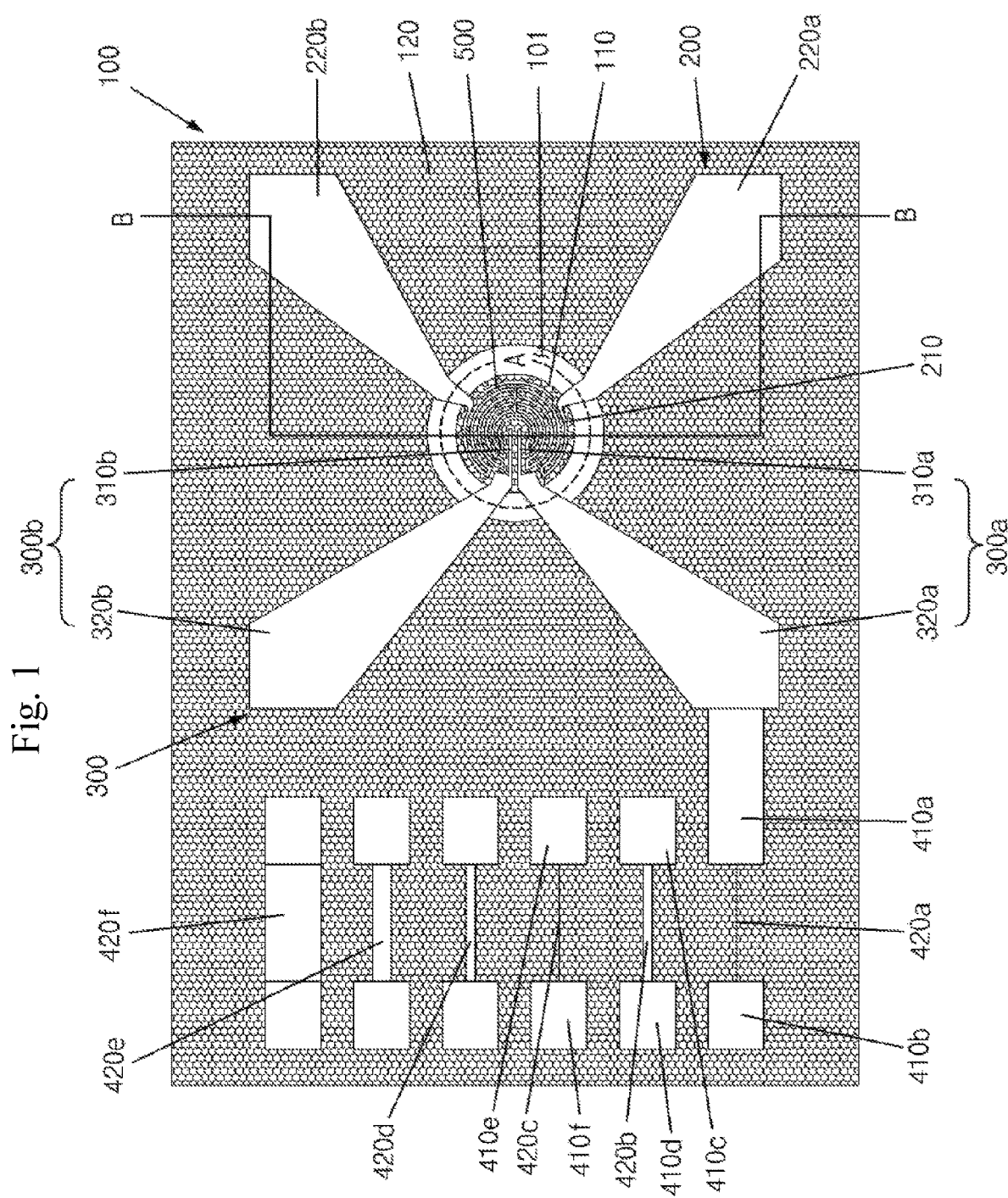
FIG. 1 is a plan view showing a micro sensor according to a first exemplary embodiment of the present invention.

Hereinbelow, exemplary embodiments of the present invention will be described in detail with reference to the accompanying drawings.

For reference, in the following descriptions, the same configurations of the present invention as those of the related art will not be described in detail. Reference is made to the foregoing descriptions of the related art.

When it is said that any part is positioned "on" another part, it means the part is directly on the other part or above the other part with at least one intermediate part. In contrast, if any part is said to be positioned "directly on" another part, it means that there is no intermediate part between the two parts.

Technical terms used here are to only describe a specific exemplary embodiment and are not intended to limit the present invention. Singular forms used here include a plurality of forms unless phrases explicitly represent an opposite meaning. A meaning of "comprising" used in a specification embodies a specific characteristic, area, integer, step, operation, element and/or component and does not exclude presence or addition of another specific characteristic, area, integer, step, operation, element, component and/or group.

Terms representing relative space of "low" and "upper" may be used for more easily describing a relationship to another portion of a portion shown in the drawings. Such terms are intended to include other meanings or operations of a using apparatus together with a meaning that is intended in the drawings. For example, when an apparatus is inverted in the drawings, any portion described as disposed at a "low" portion of other portions is described as being disposed at an "upper" portion of other portions. Therefore, an illustrative term of "low" includes entire upper and lower directions. An apparatus may rotate by 90° or another angle, and a term representing relative space is accordingly analyzed.

First Exemplary Embodiment

As shown in FIGS. 1 to 4C, according to the first exemplary embodiment, the micro sensor includes a substrate 100, a sensor electrode 300 formed on the substrate 100, and a resistance unit formed on the substrate 100, the resistance unit being electrically connected to the sensor electrode 300. The resistance unit includes at least two resistors.

When anodizing a metallic base material, an anodized film is formed. The anodized film is composed of a porous layer having several pores on the surface (upper surface) and a barrier layer existing at the lower portion of the porous layer. Here, the metallic base material may be aluminum (Al), titanium (Ti), tungsten (W), zinc (Zn), etc. It is desired that the metallic base material is made of aluminum or aluminum alloy material that is lightweight, is easy to process, is excellent in thermal conductivity, and obviates concern about heavy metal contamination.

For example, when anodizing the surface of aluminum, an alumina film is formed. The alumina film is composed of a porous alumina layer having several pores 102 penetrating the surface and a barrier layer existing at the lower portion of the porous alumina layer. According to the embodiment of the present invention, the substrate 100 may be, for example, an anodized film obtained by removing aluminum. Also, the electrode may be formed on the porous alumina layer of the alumina film, or may be formed on the barrier layer. Alternatively, the substrate 100 may be composed of only the porous alumina layer through which the pore 102 penetrates in a vertical direction by removing the barrier layer of the alumina film.

Hereinafter, the description is based on a substrate 100 where both the aluminum and the barrier layer are removed.

By removing the aluminum and the barrier layer from the anodized aluminum, the pore 102 of the substrate 100 penetrates in a vertical direction. The substrate 100 is formed of a porous alumina layer, and thus heat capacity of the micro heater is reduced.

The substrate 100 includes: a first supporting portion 110 formed in a cylindrical shape at the center of the substrate 100; a second supporting portion 120 formed at the outside by being spaced apart from the first supporting portion 110; and a bridge portion connecting the first supporting portion 110 and the second supporting portion 120. Also, several air gaps 101 are formed at the periphery of the first supporting portion 110, namely, between the first supporting portion 110 and the second supporting portion 120.

The first supporting portion 110 is provided in a cylindrical shape, and the outer circumference thereof is connected to several bridge portions.

Also, several air gaps 101 are formed at the outer circumference of the first supporting portion 110. The several air gaps 101 may be discontinuously formed. The air gaps 101 and the bridge portions are alternately placed around the first supporting portion 110. The bridge portions are formed by discontinuously forming the air gaps 101 through etching the periphery of the first supporting portion 110. Thus, a first end of each bridge portion is connected to the first supporting portion 110, and a second end thereof is connected to the second supporting portion 120.

The sensor electrode 300 is formed on the upper surface of the substrate 100.

The sensor electrode 300 detects the changes in the electrical characteristics when the gas is adsorbed onto the sensing material 600.

The sensor electrode 300 includes a first sensor electrode 300a and a second sensor electrode 300b spaced apart from the first sensor electrode 300a. The first sensor electrode 300a and the second sensor electrode 300b are spaced apart from each other, and are symmetrical based on the horizontal center line on the plane.

Each of the first and second sensor electrodes 300a and 300b includes a sensor wire formed on the first supporting portion 110 and a sensor electrode pad formed on the bridge portion and on the second supporting portion 120 by being connected to the sensor wire.

The first sensor electrode 300a includes a first sensor wire 310a formed on the upper surface of the first supporting portion 110, and a first sensor electrode pad 320a connected to the first sensor wire 310a.

The second sensor electrode 300b includes a second sensor wire 310b formed on the upper surface of the first supporting portion 110, and a second sensor electrode pad 320b connected to the second sensor wire 310b.

The sensor wire includes the first sensor wire 310a and the second sensor wire 310b. The sensor electrode pad includes the first sensor electrode pad 320a and the second sensor electrode pad 320b. The width of the sensor wire is fixed. The sensor electrode pad is placed on the upper surface of the bridge portion and the second supporting portion 120, and has the width wider than the widths of the first sensor wire 310a and the second sensor wire 310b. The widths of the sensor electrode pads of the first and the second sensor electrodes 300a and 300b are wider towards the end portions. That is, the widths of the sensor electrode pads are narrower towards the first sensor wire 310a and the second sensor wire 310b.

The sensor electrode 300 is formed of a mixture including one of or at least one of Pt, W, Co, Ni, Au, and Cu.

The heater electrode 200 is formed on the upper surface of the substrate 100.

When the electrode is formed on the porous alumina layer of the alumina film, the pore 102 placed at the lower portion of the heater electrode 200 and the sensor electrode 300 has the upper and lower portions blocked by the heater electrode 200 and the sensor electrode 300. Alternatively, when the electrode is formed on the barrier layer of the alumina film, the pore 102 placed at the lower portion of the heater electrode 200 and the sensor electrode 300 has the blocked upper portion and the opened lower portion. Alternatively, when the barrier layer of the alumina film is removed, the pore 102 placed at the lower portion of the heater electrode 200 and the sensor electrode 300 has the opened lower portion and the blocked upper portion by the heater electrode 200 and the sensor electrode 300. As described above, the heater electrode 200 is formed on the porous alumina layer, and thus heat capacity of the micro sensor is small.

The heater electrode 200 includes: a heating wire 210 closer to a sensor wire than to a sensor electrode pad by being formed on the first supporting portion 110; and a heater electrode pad formed on the second supporting portion 120 and the bridge portion by being connected to the heating wire 210.

The heating wire 210 is formed on the first supporting portion 110, and surrounds at least a part of the first sensor wire 310a and the second sensor wire 310b. The heater electrode pad includes a first heater electrode pad 220a and a second heater electrode pad 220b spaced apart from each other by respectively being connected to both ends of the heating wire 210. The heating wire 210 is placed on the upper surface of the first supporting portion 110 of the substrate 100.

When viewed in a plan view, the heating wire 210 is formed to be symmetrical about the horizontal center line of the first supporting portion 110, and includes several arc portions formed in arc shapes and several connecting portions connecting the arc portions.

The heating wire 210 includes: a first arc portion 211a formed in an arc shape close to the air gap 101; a first connecting portion 212a extending from an end of the first arc portion 211a and bent toward the inside of the first supporting portion 110; a second arc portion 211b in an arc shape extending from an end of the first connecting portion 212a and spaced apart from the first arc portion 211a inwards; a second connecting portion 212b extending from an end of the second arc portion 211b toward the inside of the first supporting portion 110; and a third arc portion 211c. In this manner, several arc portions and connecting portions are formed by being repeatedly connected to each other.

The heating wire 210 is connected from the first arc portion 211a to the third arc portion 211c to have an integral body, and is symmetrical about the horizontal center line of the first supporting portion 110.

Figure 2:
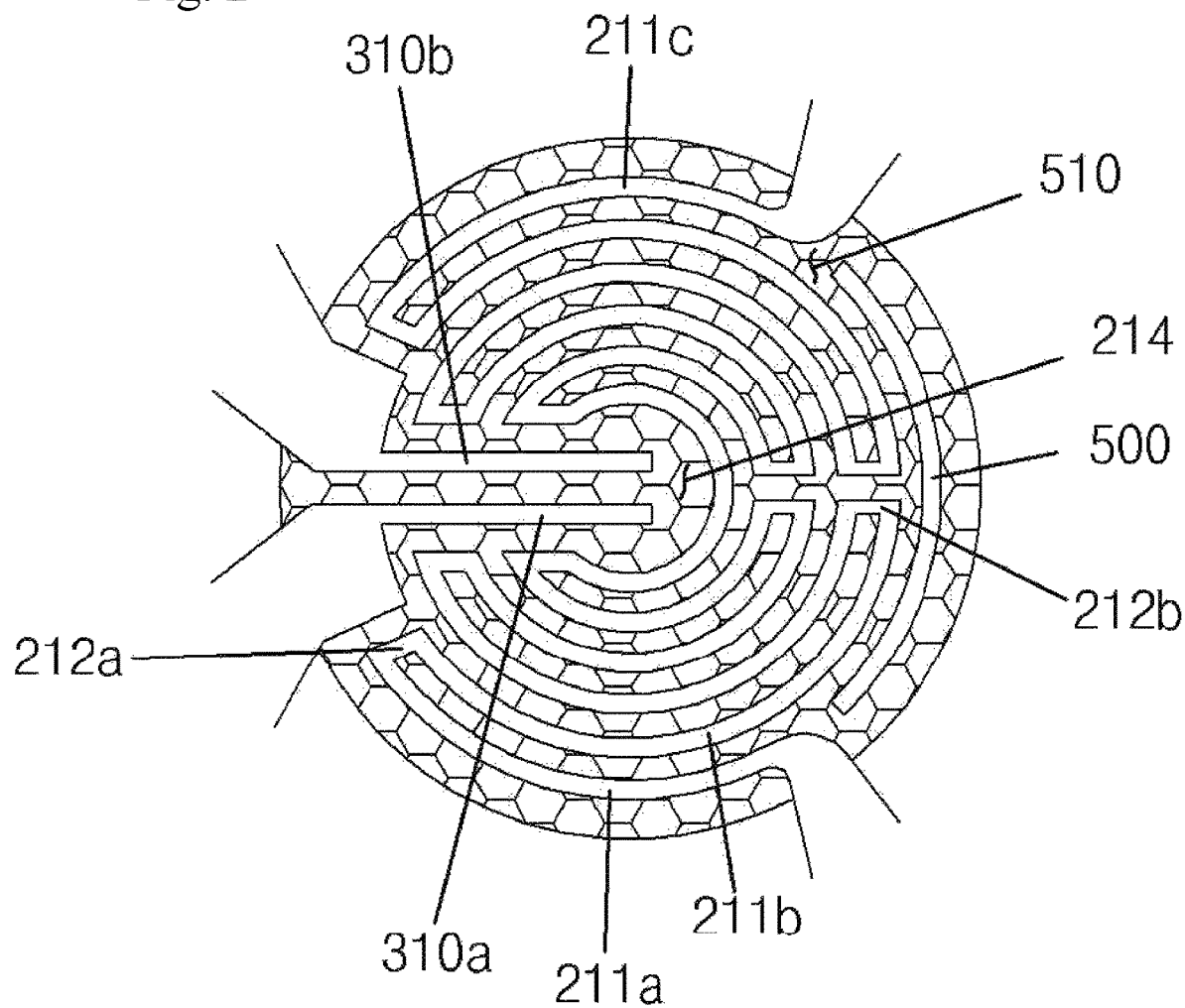
FIG. 2 is an enlarged view of A portion of FIG. 1.

As shown in FIG. 2, several arc portions of the heating wire 210 are formed in a half-arc shape. Thus, the heating wire 1210 is overall in a circular shape. Accordingly, temperature uniformity of the first supporting portion 110 may be enhanced.

The central portion of the heating wire 210 is a point where opposite arc portions meet, and the central point is in a left side opened circular shape by joining two arc portions in arc shapes together. An isolated space portion 214 is formed inside of the central portion. The isolated space portion 214 is formed by extending from the central portion of the heating wire 210 to the left of the heating wire 210. That is, to form the isolated space portion 214 from the left center to the central portion of the heating wire 210, arc portions are spaced apart from each other. The sensor wire is placed at the isolated space portion 214. That is, the heating wire 210 surrounds at least a part of the first and the second sensor wires 310a and 310b. Also, a second end portion of the first arc portion 211a is connected to the first heater electrode pad 220a, and a first end portion of the third arc portion 211c is connected to the second heater electrode pad 220b.

The heater electrode 200 is formed of a mixture including one or at least one of Pt, W, Co, Ni, Au, and Cu.

In the meantime, a dummy metal 500 is formed between both ends of the heating wire 210, namely, the ends of the first arc portion 211a and the third arc portion 211c respectively connected to the first heater electrode pad 220a and the second heater electrode pad 220b.

The dummy metal 500 is formed in an arc shape between the air gap 101 and the heating wire 210 of the heater electrode 200. The dummy metal 500 is spaced apart from the heating wire 210 adjacent thereto.

It is desired that the dummy metal 500 is formed outside of the heating wire 210 and is a metal. The material of the dummy metal 500 may be the same as the electrode material, and the electrode material may be a metal such as platinum, aluminum, copper, etc.

The central angles of the first arc portion 211a and the third arc portion 211c are small, compared to the remaining arc portions placed inside thereof. At the outer circumference of the heating wire 210, a space 510 is defined between the ends of the first arc portion 211a and the third arc portion 211c. The dummy metal 500 is placed at the space 510.

The space 510 at the outer circumference of the heating wire 210 is partially filled by the area of the dummy metal 500. Thus, when viewed in a plan view, the outer circumference of the heating wire 210 and the dummy metal 500 is in a circular shape, whereby temperature uniformity of the first supporting portion 110 may be enhanced. Accordingly, temperature distribution of the heating wire 210, which is heated by low power, on the first supporting portion 110 is more uniform.

The heater electrode pad includes the first and the second heater electrode pads 220a and 220b that are respectively connected to both ends of the heating wire 210. As described above, at least two heater electrode pads are formed. The widths of the heater electrode pads are wider towards the outside. That is, the widths of the heater electrode pads are narrower towards the heating wire 210. The width of the heater electrode pad is wider than the width of the heating wire 210.

The heater electrode pad and the sensor electrode pad are placed in radial directions with respect to the first supporting portion 110.

The heater electrode pad is placed at the right of the substrate 100, the sensor electrode pad is placed at the central portion of the substrate 100, and the resistance unit, described below, is placed at the left side of the substrate 100.

An anti-discoloration protective layer (not shown) is formed on a part of an upper portion of the heater electrode 200 and the sensor electrode 300. The anti-discoloration protective layer may be formed of oxide type material. Moreover, the anti-discoloration protective layer may be formed of at least one of tantalum oxide (TaOx), titanium oxide ($TiO_2$), silicon oxide ($SiO_2$), and aluminum oxide ($Al_2O_3$).

The air gap 101 formed on the substrate 100 surrounds the heating wire 210 and the first and the second sensor wires 310a and 310b. The air gap 101 is placed at the circumference of the first supporting portion 110, namely, the circumference of the heating wire 210 and the first and the second sensor wires 310a and 310b. The air gap 101 is placed at the sides of the heating wire 210 and the first and the second sensor wires 310a and 310b.

The maximum width (lateral width) of the air gap 101 is wider than the maximum width of the pore 102. The air gap 101 is formed in the arc shape, and four air gaps are formed. The several air gaps 101 are spaced apart from each other in a circumferential direction. That is, several air gaps 101 are discontinuously formed.

Specifically, the air gaps 101 are placed between the first heater electrode pad 220a and the first sensor electrode pad 320a of the first sensor electrode 300a, between the first heater electrode pad 220a and the second heater electrode pad 220b, between the second heater electrode pad 220b and the second sensor electrode pad 320b of the second sensor electrode 300b, and between the second sensor electrode pad 320b of the second sensor electrode 300b and the first sensor electrode pad 320a of the first sensor electrode 300a. That is, the air gaps 101 are formed at an area except for the portion supporting the heater electrode 200 and the sensor electrode 300.

The air gap 101 is formed penetrating in the vertical direction. That is, the air gap 101 is a space formed by penetrating from the upper surface to the lower surface of the substrate 100.

Due to the air gap 101, on the substrate 100, formed are the first supporting portion 110 supporting the heating wire 210 and the sensor wire in common; and the second supporting portion 120 and the bridge portion that supports the heater electrode pad and the sensor electrode pad. That is, the air gap 101 is formed between the first supporting portion 110 and the second supporting portion 120. Accordingly, the air gaps 101 and the bridge portions are alternately placed around the first supporting portion 110.

When viewed in a plan view, the first supporting portion 110 is formed in a circular shape, and is surrounded by the air gap 101. The area of the first supporting portion 110 is wider than the area of the heating wire 210 and the sensor wire.

The first supporting portion 110 and the second supporting portion 120 are connected to each other via the bridge portion.

Also, the first supporting portion 110 and the second supporting portion 120 are spaced apart from each other due to the air gap 101 at the portion other than the bridge portion. Accordingly, the first supporting portion 110 and the second supporting portion 120 are connected to each other at four portions due to four bridge portions.

On the first supporting portion 110, a sensing material 600 is formed to cover the heating wire 210 and the sensor wire. That is, the sensing material 600 is formed at a position corresponding to the first supporting portion 110. The sensing material 600 is formed by being printed. When the sensing material 600 is printed, the print in a mesh-net shape remains on the surface of the sensing material 600 after forming the sensing material 600.

The resistance unit is formed on the substrate 100, and is electrically connected to the sensor electrode pad of the sensor electrode 300.

The resistance unit is formed on the upper surface of the substrate 100, and thus the resistance unit is formed on the same surface as the sensor electrode 300.

The resistance unit is spaced apart from the heater electrode 200.

The resistance unit is placed on the second supporting portion 120. According to the micro sensor of the embodiment, a gas sensing portion (the sensor electrode and the heater electrode) is placed at the right side of the substrate 100, and the resistance unit is placed at the left side of the substrate 100. Accordingly, the air gap 101 is placed between the resistance unit and the first supporting portion 110.

The resistance unit includes at least two resistors.

At least one of the resistors is a sheet resistor or is formed in a fine-pattern (line) shape, thereby minimizing the volume of the resistance unit.

Specifically, the resistance unit includes a first, a second, a third, a fourth, a fifth, and a sixth resistance pad 410a, 410b, 410c, 410d, 410e, and 410f and a first, a second, and a third resistor 420a, 420b, and 420c.

The resistance pads are spaced apart from each other.

The first resistance pad 410a is connected to the first sensor electrode pad 320a of the sensor electrode 300. Alternatively, the first resistance pad 410a may be connected to the second sensor electrode pad 320b of the sensor electrode 300.

The first resistance pad 410a of the resistance unit being connected to the sensor electrode 300 may be formed with the first sensor electrode pad 320a or the second sensor electrode pad 320b of the sensor electrode 300 as an integral body.

The first resistance pad 410a is connected to at least one resistance pad via at least one resistor.

A first end of the first resistor 420a is connected to the first resistance pad 410a, and a second end of the first resistor 420a is connected to the second resistance pad 410b.

A first end of the second resistor 420b is connected to the third resistance pad 410c, and a second end of the second resistor 420b is connected to the fourth resistance pad 410d.

A first end of the third resistor 420c is connected to the fifth resistance pad 410e, and a second end of the third resistor 420c is connected to the sixth resistance pad 410f.

In the embodiment, the resistance unit may include six resistors. The resistance unit includes a first, a second, a third, a fourth, a fifth, and a sixth resistor 420a, 420b, 420c, 420d, 420e, and 420f.

In the embodiment, opposite ends of each resistor are provided with respective resistance pads. Accordingly, the first ends and the second ends of the remaining resistors, i.e., the fourth, the fifth, and the sixth resistors 420d, 420e, and 420f are provided with respective resistance pads.

The six resistors have different resistance values, or at least two of the six resistors have different resistance values.

The first resistor 420a connected to the first sensor electrode pad 320a of the sensor electrode 300 may have the largest value of the six resistance values of the six resistors. The first, the second, the third, the fourth, the fifth, and the sixth resistors 420a, 420b, 420c, 420d, 420e, and 420f are sheet resistors. When the line width is narrow, the resistance value is large, and when the line width is wide, the resistance value is small.

The resistance unit is connected to only the first sensor electrode pad 320a of the sensor electrode 300, and thus the sensor electrode 300 is connected to the resistance unit in series.

Respective resistance pads may be selectively connected to the sensor electrode 300 through wire bonding 700, etc. depending on the resistance of the sensing material 600.

Figure 4C:
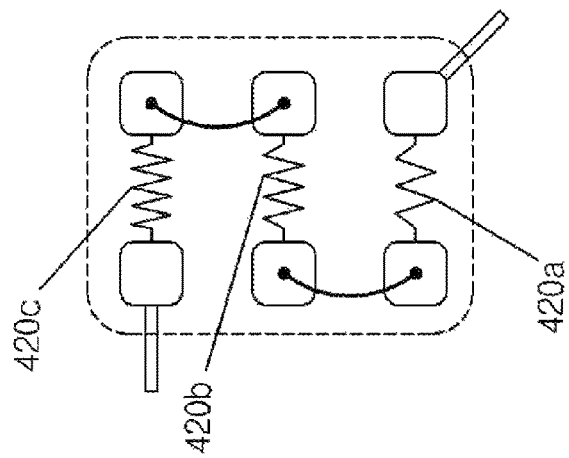
FIGS. 4A to 4C are schematic views showing changes of a resistance value of a resistance unit of the micro sensor according to the first exemplary embodiment of the present invention.
Figure 4B:
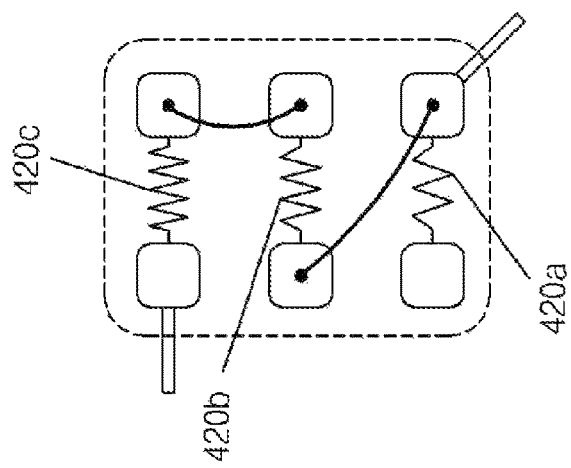
Figure 4A:
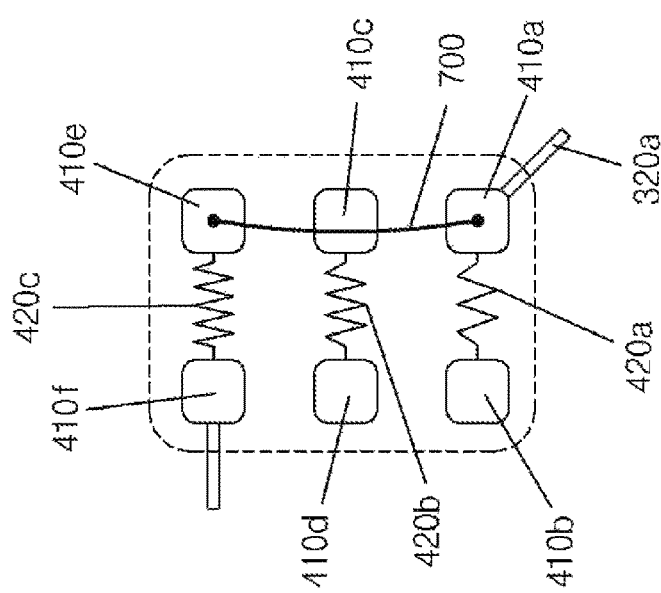

As shown in FIGS. 4A to 4C, respective resistance pads may have different resistance values through wire bonding 700 in different ways.

FIG. 4A shows a case of using only the third resistor 420c. In this case, the first resistance pad 410a connected to the first sensor electrode pad 320a is connected to the fifth resistance pad 410e through wire bonding 700, and the sixth resistance pad 410f is connected to the out.

FIG. 4B shows a case of using the second resistor 420b and the third resistor 420c connected to the second resistor 420b in series. The resistance value of the resistance unit is the sum of resistance values of the second resistor 420b and the third resistor 420c. In this case, the first resistance pad 410a connected to the first sensor electrode pad 320a is connected to the fourth resistance pad 410d through wire bonding 700, and the third resistance pad 410c is connected to the fifth resistance pad 410e through wire bonding 700, and the sixth resistance pad 410f is connected to the out.

FIG. 4C shows a case of using the first resistor 420a, the second resistor 420b connected to the first resistor 420a in series, and the third resistor 420c connected to the second resistor 420b in series. The resistance value of the resistance unit is the sum of resistance values of the first resistor 420a, the second resistor 420b, and the third resistor 420c. In this case, the first resistance pad 410a connected to the first sensor electrode pad 320a is connected to the second resistance pad 410b, and the second resistance pad 410b is connected to the fourth resistance pad 410d, the third resistance pad 410c is connected to the fifth resistance pad 410e, and the sixth resistance pad 410f is connected to the out.

As described above, at least two of the resistors may be connected to each other in series.

Hereinafter, the operation of the embodiment having the above-described configuration will be disclosed.

In order to measure the gas concentration, first, the same electric power is applied to two heater electrode pad 220 of the heater electrode 200 so as to heat the sensing material 600 to the constant temperature.

Ambient gas is adsorbed onto or desorbed from the heated sensing material 600.

Accordingly, electrical conductivity between the first sensor wire 310a and the second sensor wire 310b changes, and this sensing signal is amplified through the resistance unit, thereby detecting gas.

Also, for more precise measurement, target gas concentration is measured after resetting the sensing material 600 to its initial state through high temperature heating, thereby forcibly removing gas species or moisture being already adsorbed onto the sensing material 600.

Second Exemplary Embodiment

Hereinafter, the micro sensor according to the second exemplary embodiment of the present invention will be disclosed.

In describing the micro sensor according to the second exemplary embodiment, the same reference numerals denote the same or similar configurations to those of the micro sensor according to the first exemplary embodiment, and detailed descriptions thereof will be omitted.

Figure 5:
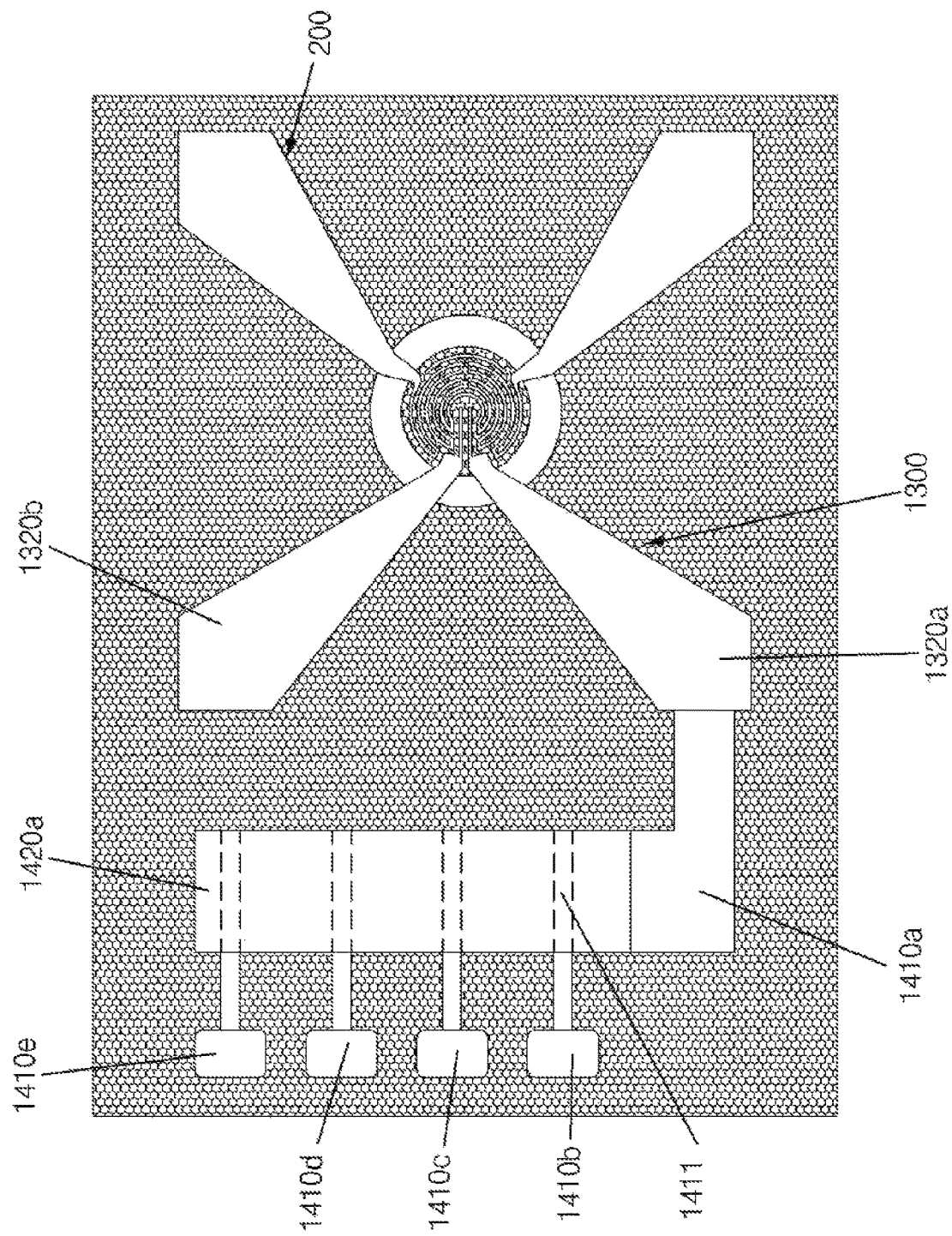
FIG. 5 is a plan view showing a micro sensor according to a second exemplary embodiment of the present invention.

As shown in FIG. 5, according to the second exemplary embodiment, the resistance unit of the micro sensor includes a first, a second, a third, a fourth, and a fifth resistance pad 1410a, 1410b, 1410c, 1410d, and 1410e and a first resistor 1420a.

The first resistor 1420a is formed in a long band shape in the longitudinal direction. The first resistor 1420a is placed at the left of the sensor electrode 1300.

The first resistor 1420a is formed of at least one of NiCr, AgMn, CuNi, Ta, TaSi, and C. The first resistor 1420a may be formed of different material from the heater electrode 200 or the sensor electrode 1300.

The first resistance pad 1410a is formed in a lateral direction between the first sensor electrode pad 1320a and the first resistor 1420a.

The right end of the first resistance pad 1410a is connected to the first sensor electrode pad 1320a or the second sensor electrode pad 1320b of the sensor electrode 1300. The left end of the first resistance pad 1410a is connected to the front end of the first resistor 1420a.

A least one of the second resistance pad 1410b and the third resistance pad 1410c includes both the pad electrode portion 1411 of which at least a part is connected to the first resistor 1420a, and a bonding portion connected to the pad electrode portion 1411, the bonding portion being formed at a portion other than the first resistor 1420a.

In the embodiment, each of the second, the third, the fourth, and the fifth resistance pads 1410b, 1410c, 1410d, and 1410e includes the pad electrode portion 1411 and the bonding portion.

The pad electrode portion 1411 is placed at the right of the bonding portion.

The longitudinal width of the pad electrode portion 1411 is narrower than that of the bonding portion.

The pad electrode portion 1411 is formed long in a lateral direction. The lateral length of the pad electrode portion 1411 is longer than the lateral length of the first resistor 1420a, and thus the first resistor 1420a and the bonding portion are spaced apart from each other in the lateral direction.

The pad electrode portion 1411 is in contact with the first resistor 1420a by intersecting with the first resistor 1420a, whereby the pad electrode portion 1411 is in contact with opposite ends of the first resistor 1420a. In the embodiment, the pad electrode portion 1411 is in contact with the left and the right ends of the first resistor 1420a by intersecting with the first resistor 1420a in the lateral direction.

To place the first resistor 1420a on the upper portion of the pad electrode portion 1411, the first resistor 1420a is formed after forming the resistance pads.

Each pad electrode portion 1411 is spaced apart from the first resistance pad 1410a in the longitudinal direction. From the second resistance pad 1410b to the fifth resistance pad 1410e, the distance between each pad electrode portion 1411 and the first resistance pad 1410a increases. Depending on the distance between each pad electrode portion 1411 and the first resistance pad 1410a, the resistance value changes. Accordingly, the resistance values may selectively differ.

Also, through wire bonding of the boding portion of each resistance pad, the resistors may be connected to each other in parallel.

Third Exemplary Embodiment

Hereinafter, the micro sensor according to the third exemplary embodiment of the present invention will be disclosed.

In describing the micro sensor according to the third exemplary embodiment, the same reference numerals denote the same or similar configurations to those of the micro sensor according to the first exemplary embodiment, and detailed descriptions thereof will be omitted.

Figure 6:
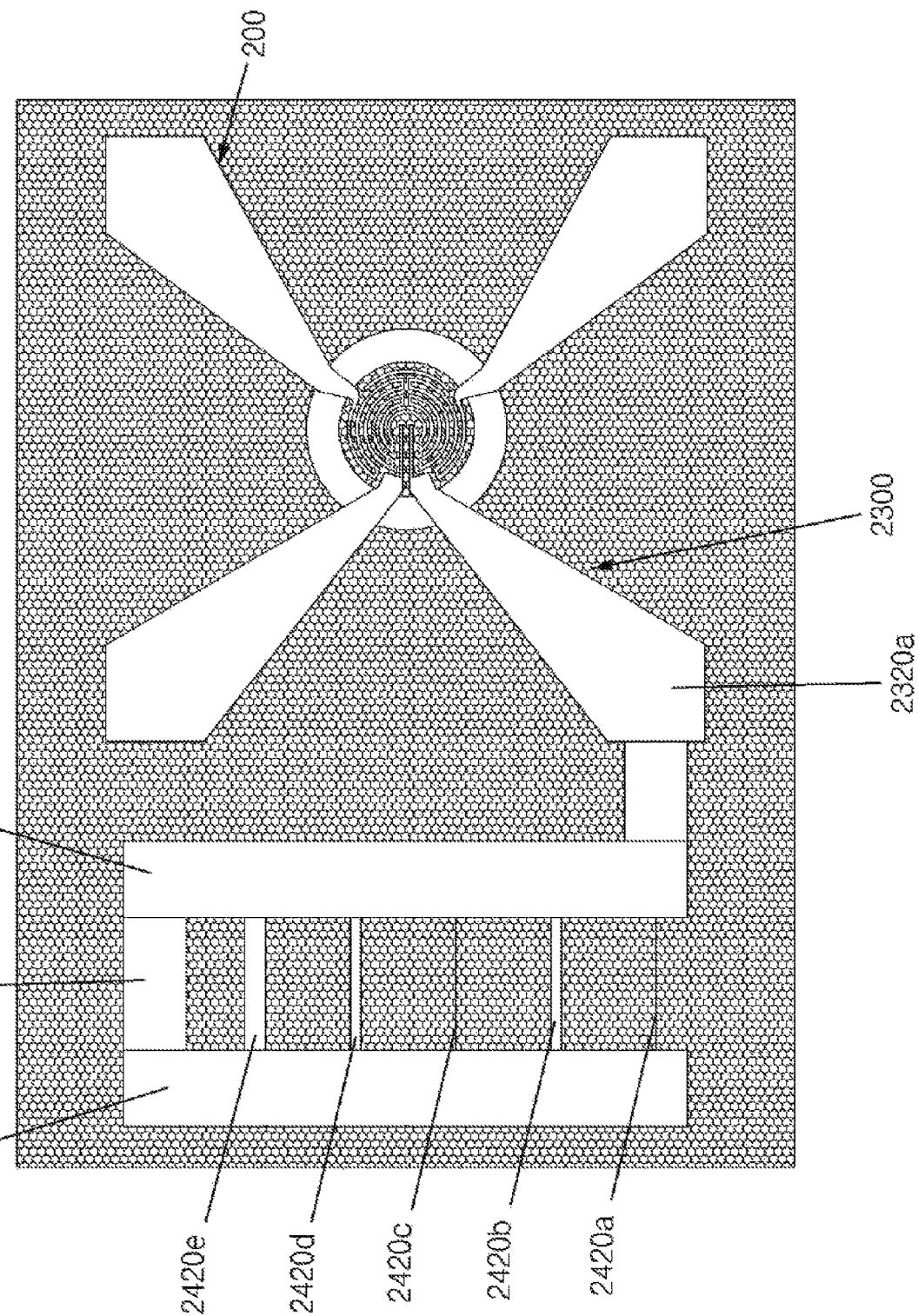
FIG. 6 is a plan view showing a micro sensor according to a third exemplary embodiment of the present invention.

As shown in FIG. 6, according to the third exemplary embodiment, the resistance unit of the micro sensor includes at least two resistors connected to each other in parallel.

The resistance unit includes a first and a second resistance pad 2410a and 2410b and a first, a second, a third, a fourth, a fifth, and a sixth resistor 2420a, 2420b, 2420c, 2420d, 2420e, and 2420f.

The first resistance pad 2410a is connected to the first sensor electrode pad 2320a of the sensor electrode 2300.

The first resistance pad 2410a is placed at the right of the first, the second, the third, the fourth, the fifth, and the sixth resistors 2420a, 2420b, 2420c, 2420d, 2420e, and 2420f.

A first end of the first resistor 2420a is connected to the first resistance pad 2410a, and a second end of the first resistor 2420a is connected to the second resistance pad 2410b.

The second resistance pad 2410b is placed at the left of the first, the second, the third, the fourth, the fifth, and the sixth resistors 2420a, 2420b, 2420c, 2420d, 2420e, and 2420f.

A first end of the second resistor 2420b is connected to the first resistance pad 2410a, and a second end of the second resistor 2420b is connected to the second resistance pad 2410b.

In the same manner, first ends of the third, the fourth, the fifth, and the sixth resistors 2420c, 2420d, 2420e, and 2420f are connected to the first resistance pad 2410a, and second ends thereof are connected to the second resistance pad 2410b.

As described above, several resistors are connected to each other in parallel on the substrate.

In this case, in order to adjust the resistance values of the resistance unit, the unnecessary resistor is scraped off according to the sensing material during use. Accordingly, the resistance value can be adjusted through the simple operation without wire bonding.

Fourth Exemplary Embodiment

Hereinafter, the micro sensor according to the fourth exemplary embodiment of the present invention will be disclosed.

In describing the micro sensor according to the fourth exemplary embodiment, the same reference numerals denote the same or similar configurations to those of the micro sensor according to the first exemplary embodiment, and detailed descriptions thereof will be omitted.

Figure 7:
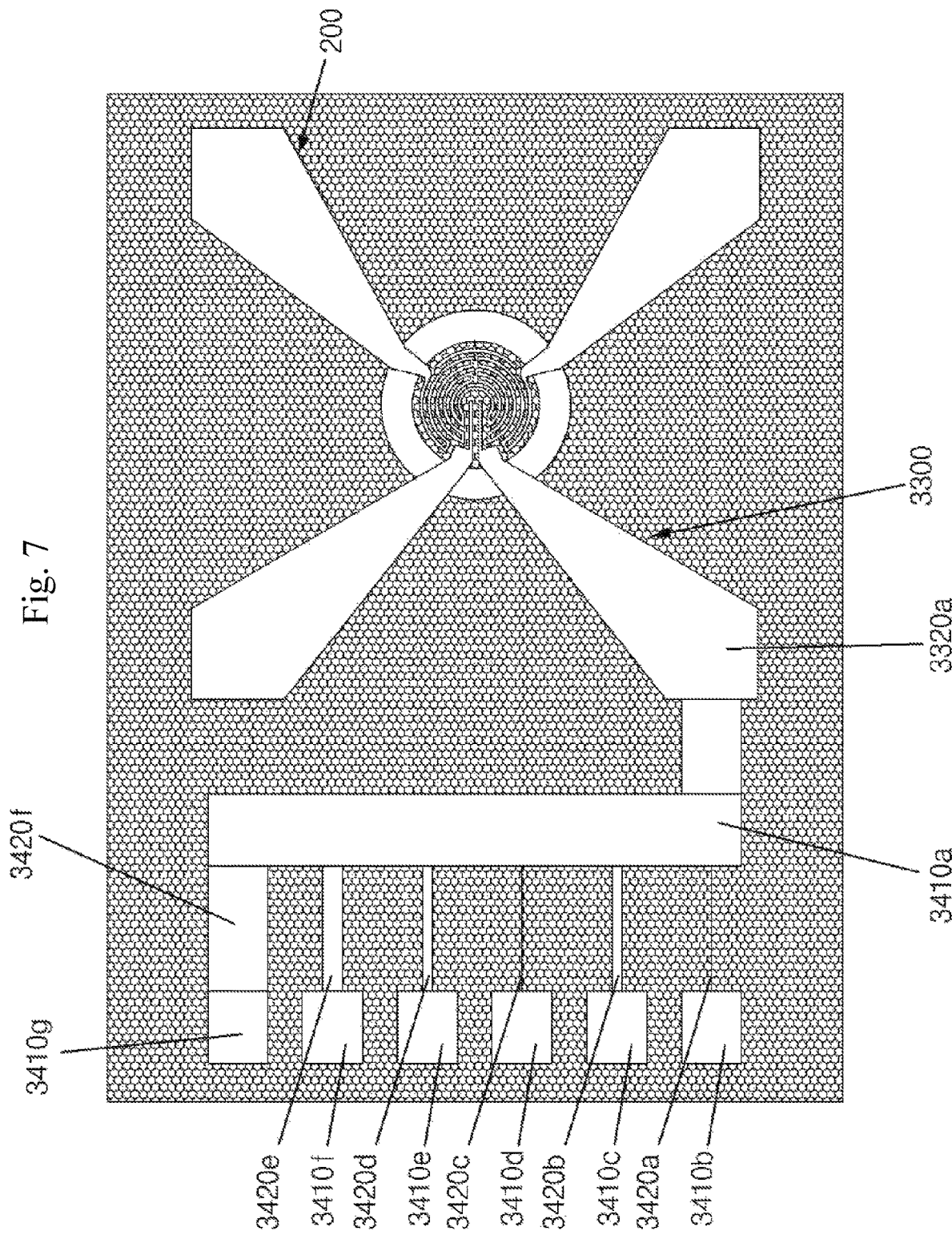
FIG. 7 is a plan view showing a micro sensor according to a fourth exemplary embodiment of the present invention.

As shown in FIG. 7, according to the fourth exemplary embodiment, the resistance unit of the micro sensor includes a first, a second, a third, a fourth, a fifth, a sixth, and a seventh resistance pad 3410a, 3410b, 3410c, 3410d, 3410e, 3410f, and 3410g and a first, a second, a third, a fourth, a fifth, and a sixth resistor 3420a, 3420b, 3420c, 3420d, 3420e, and 3420f.

The first resistance pad 3410a is connected to the first sensor electrode pad 3320a of the sensor electrode 3300.

The first resistance pad 3410a is placed at the right of the first, the second, the third, the fourth, the fifth, and the sixth resistors 3420a, 3420b, 3420c, 3420d, 3420e, and 3420f.

A first end of the first resistor 3420a is connected to the first resistance pad 3410a, and a second end of the first resistor 3420a is connected to the second resistance pad 3410b.

The second, the third, the fourth, the fifth, the sixth, and the seventh resistance pads 3410b, 3410c, 3410d, 3410e, 3410f, and 3410g are placed at the left of the first, the second, the third, the fourth, the fifth, and the sixth resistors 3420a, 3420b, 3420c, 3420d, 3420e, and 3420f.

A first end of the second resistor 3420b is connected to the first resistance pad 3410a, and a second end of the second resistor 3420b is connected to the third resistance pad 3410c.

In the same manner, first ends of the third, the fourth, the fifth, and the sixth resistors 3420c, 3420d, 3420e, and 3420f are connected to the first resistance pad 3410a, and second ends thereof are connected to the fourth, the fifth, the sixth, and the seventh resistance pads 3410d, 3410e, 3410f, and 3410g.

Accordingly, through wire bonding on only the resistance pad connected to the second end of the required resistor, the resistance value can be adjusted.

Fifth Exemplary Embodiment

Hereinafter, the micro sensor according to the fifth exemplary embodiment of the present invention will be disclosed.

In describing the micro sensor according to the fifth exemplary embodiment, the same reference numerals denote the same or similar configurations to those of the micro sensor according to the first exemplary embodiment, and detailed descriptions thereof will be omitted.

Figure 8:
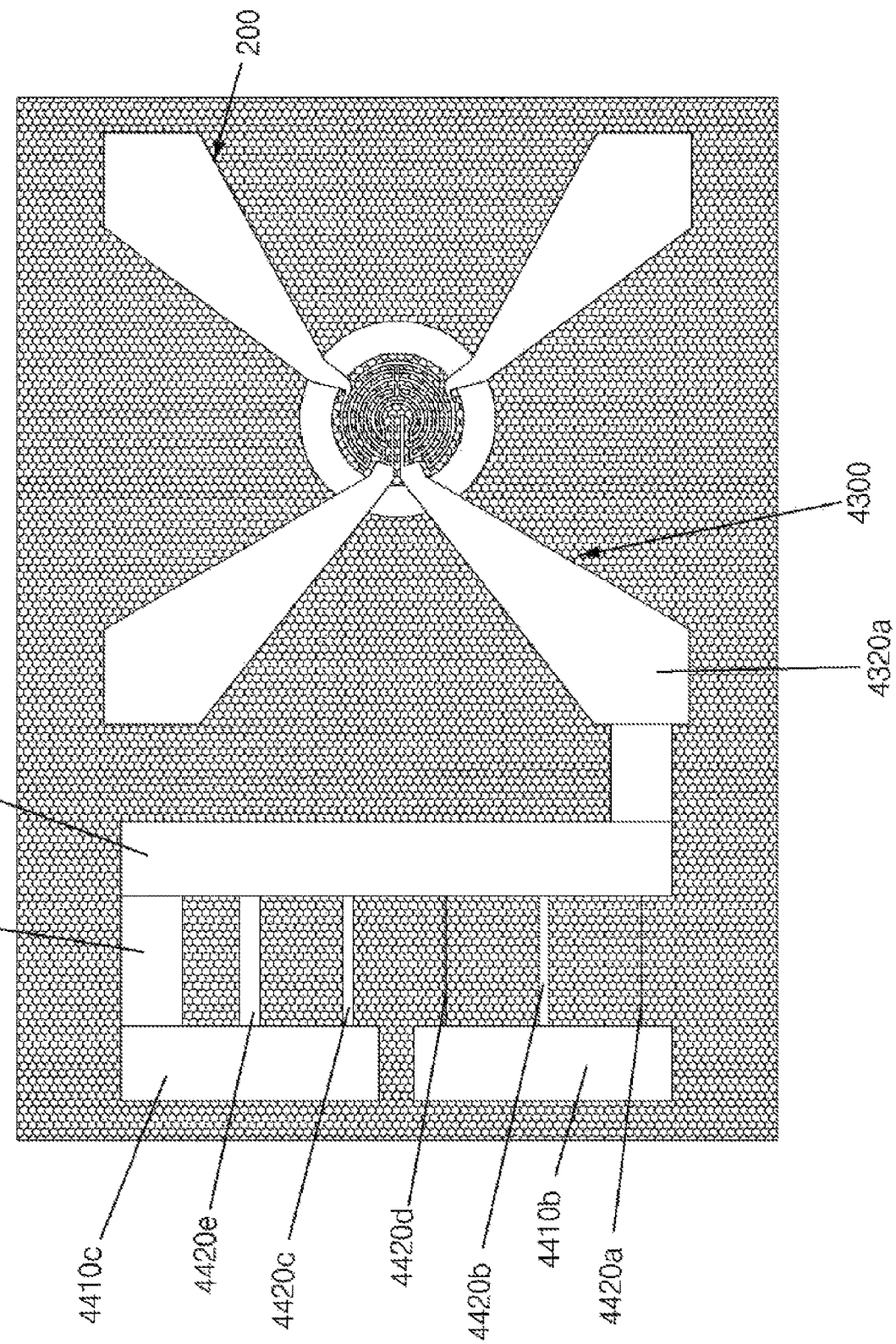
FIG. 8 is a plan view showing a micro sensor according to a fifth exemplary embodiment of the present invention.

As shown in FIG. 8, according to the fifth exemplary embodiment, the resistance unit of the micro sensor includes a first, a second, and a third resistance pad 4410a, 4410b, and 4410c and a first, a second, a third, a fourth, a fifth, and a sixth resistor 4420a, 4420b, 4420c, 4420d, 4420e, and 4420f.

The first resistance pad 4410a is connected to the first sensor electrode pad 4320a of the sensor electrode 4300.

The first resistance pad 4410a is placed at the right of the first, the second, the third, the fourth, the fifth, and the sixth resistors 4420a, 4420b, 4420c, 4420d, 4420e, and 4420f.

First ends of the first, the second, and the fourth resistors 4420a, 4420b, 4420d are connected to the first resistance pad 4410a, and second ends of the first, the second, and the fourth resistors 4420a, 4420b, and 4420d are connected to the second resistance pad 4410b.

The second resistance pad 4410b is placed at the left of the first, the second, and the fourth resistors 4420a, 4420b, and 4420d.

First ends of the third, the fifth, and the sixth resistors 4420c, 4420e, and 4420f are connected to the first resistance pad 4410a, and second ends of the third, the fifth, and the sixth resistors 4420c, 4420e, 4420f are connected to the third resistance pad 4410c.

The third resistance pad 4410c is placed at the left of the third, the fifth, and the sixth resistors 4420c, 4420e, and 4420f.

The sum of the resistance values of the third, the fifth, and the sixth resistors 4420c, 4420e, and 4420f is different from the sum of the resistance values of the first, the second, and the fourth resistors 4420a, 4420b, and 4420d.

Sixth Exemplary Embodiment

Hereinafter, the micro sensor according to the sixth exemplary embodiment of the present invention will be disclosed.

In describing the micro sensor according to the sixth exemplary embodiment, the same reference numerals denote the same or similar configurations to those of the micro sensor according to the first exemplary embodiment, and detailed descriptions thereof will be omitted.

Figure 9:
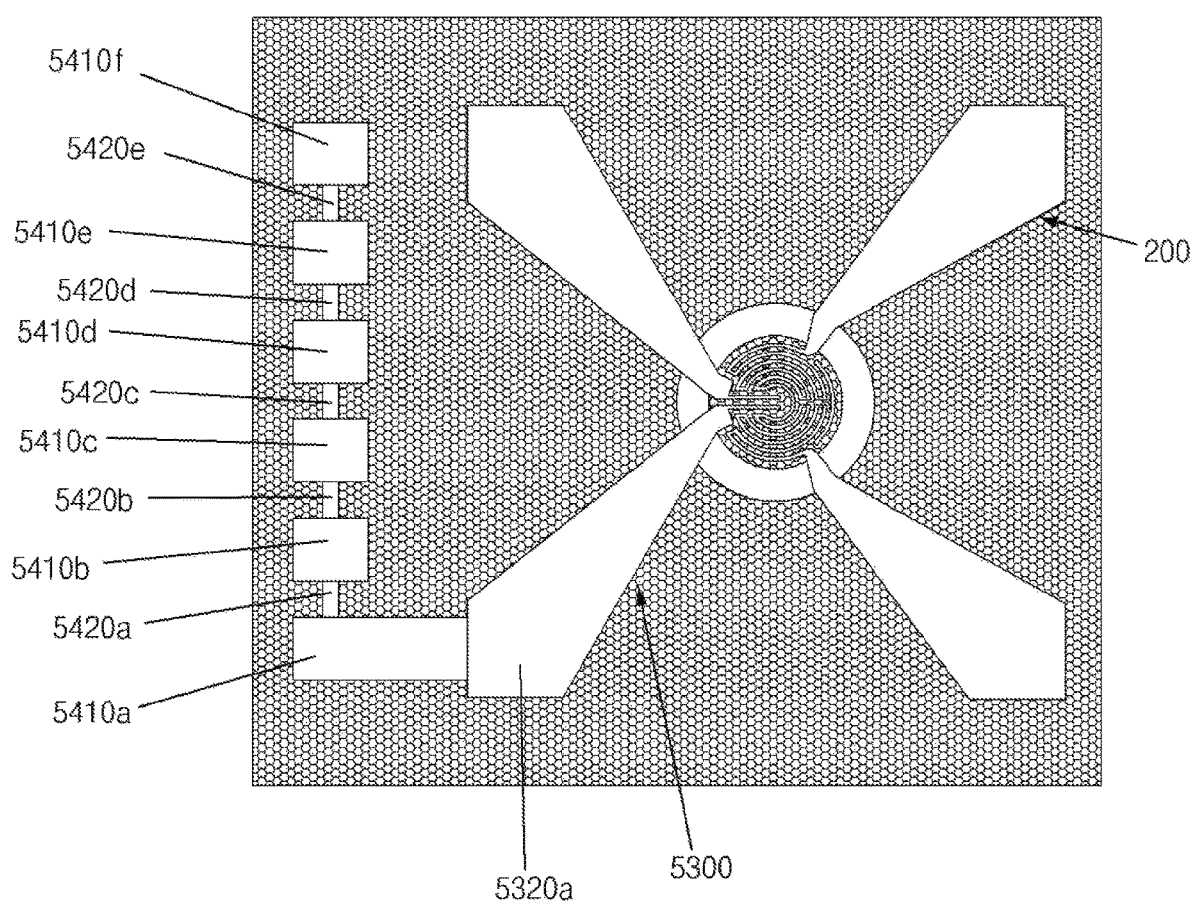
FIG. 9 is a plan view showing a micro sensor according to a sixth exemplary embodiment of the present invention.

As shown in FIG. 9, according to the sixth exemplary embodiment, the resistance unit of the micro sensor includes at least two resistors connected to each other in series.

The resistance unit includes a first, a second, a third, a fourth, a fifth, and a sixth resistance pad 5410a, 5410b, 5410c, 5410d, 5410e, and 5410f a first, a second, a third, a fourth, and a fifth resistor 5420a, 5420b, 5420c, 5420d, and 5420e.

The first resistance pad 5410a is connected to the first sensor electrode pad 5320a of the sensor electrode 5300.

A first end of the first resistor 5420a is connected to the first resistance pad 5410a, and a second end of the first resistor 5420a is connected to the second resistance pad 5410b.

A first end of the second resistor 5420b is connected to the second resistance pad 5410b, and a second end of the second resistor 5420b is connected to the third resistance pad 5410c.

In the same manner, the third, the fourth, and the fifth resistors 5420c, 5420d, and 5420e are sequentially connected to the third, the fourth, the fifth, and the sixth resistance pads 5410c, 5410d, 5410e, 5410f in series.

The resistance unit may be used by connecting the second, the third, the fourth, the fifth, and the sixth resistance pads 5410b, 5410c, 5410d, 5410e, and 5410f to the out depending on the resistance of the sensing material.

As described above, although the exemplary embodiments of the present invention have been disclosed, those skilled in the art will appreciate that various modifications or changes are possible, without departing from the scope and spirit of the invention as disclosed in the accompanying claims.

What is claimed is:

1. A micro sensor for sensing gas, the micro sensor comprising:
    a substrate;
    a sensing material provided on the substrate;
    a heater electrode provided on the substrate for heating the sensing material;
    a sensor electrode provided on the substrate for detecting a change of an electrical characteristic when the gas is adsorbed onto the sensing material heated by the heater electrode; and
    a resistance unit including at least two resistors and provided on the substrate, the resistance unit being electrically connected to the sensor electrode,
    wherein a resistance value of the resistance unit is adjusted by connecting the at least two resistors using wire bonding or by cutting off an unnecessary resistor among the at least two resistors that are connected in advance, depending on the sensing material.

2. The micro sensor of claim 1, wherein at least two of the at least two resistors have different resistance values.

3. The micro sensor of claim 1, wherein the resistance unit includes a first, a second, and a third resistance pad and a first resistor,
    the first resistance pad is connected to the sensor electrode,
    at least one of the second resistance pad and the third resistance pad includes both a pad electrode portion of which at least a part is connected to the first resistor and a bonding portion connected to the pad electrode portion, the bonding portion being provided on the substrate at a portion other than the first resistor, and
    the pad electrode portion is in contact with the first resistor by intersecting with the first resistor, whereby the pad electrode portion is in contact with opposite ends of the first resistor.

4. The micro sensor of claim 3, wherein the first resistor is provided on an upper portion of the pad electrode portion.

5. The micro sensor of claim 1, wherein one of the at least two resistors is formed of any one of NiCr, AgMn, CuNi, Ta, TaSi, and C.

6. The micro sensor of claim 1, wherein the resistance unit includes a first, a second, a third, and a fourth resistance pad and a first and a second resistor,
    the first resistance pad is connected to the sensor electrode,
    a first end of the first resistor is connected to the first resistance pad,
    a second end of the first resistor is connected to the second resistance pad,
    a first end of the second resistor is connected to the third resistance pad, and
    a second end of the second resistor is connected to the fourth resistance pad.

7. The micro sensor of claim 1, wherein the resistance unit includes a first, a second, and a third resistance pad and a first and a second resistor,
    the first resistance pad is connected to a first sensor electrode pad of the sensor electrode,
    the second resistance pad or the third resistance pad is connected to a second sensor electrode pad of the sensor electrode,
    a first end of the first resistor is connected to the first resistance pad,
    a second end of the first resistor is connected to the second resistance pad,
    a first end of the second resistor is connected to the first resistance pad, and
    a second end of the second resistor is connected to the third resistance pad.

8. The micro sensor of claim 1, wherein the resistance unit includes a first and a second resistance pad and a first and a second resistor,
    the first resistance pad is connected to the sensor electrode,
    a first end of the first resistor is connected to the first resistance pad,
    a second end of the first resistor is connected to the second resistance pad,
    a first end of the second resistor is connected to the first resistance pad, and
    a second end of the second resistor is connected to the second resistance pad.

9. The micro sensor of claim 1, wherein the resistance unit includes a first, a second, and a third resistance pad and a first and a second resistor,
    the first resistance pad is connected to the sensor electrode,
    a first end of the first resistor is connected to the first resistance pad,
    a second end of the first resistor is connected to the second resistance pad,
    a first end of the second resistor is connected to the first resistance pad, and
    a second end of the second resistor is connected to the third resistance pad.

10. The micro sensor of claim 1, wherein the resistance unit includes a first, a second, and a third resistance pad and a first, a second, and a third resistor,
    the first resistance pad is connected to the sensor electrode,
    first ends of the first and the second resistors are connected to the first resistance pad,
    second ends of the first and the second resistors are connected to the second resistance pad, a first end of the third resistor is connected to the first resistance pad, and a second end of the third resistor is connected to the third resistance pad.

11. The micro sensor of claim 1, wherein the resistance unit includes a first, a second, and a third resistance pad and a first and a second resistor, the first resistance pad is connected to the sensor electrode, a first end of the first resistor is connected to the first resistance pad, a second end of the first resistor is connected to the second resistance pad, a first end of the second resistor is connected to the second resistance pad, and a second end of the second resistor is connected to the third resistance pad.

12. The micro sensor of claim 1, wherein the heater electrode includes a heating wire closer to a sensor wire than to a sensor electrode pad of the sensor electrode.

13. The micro sensor of claim 12, wherein the substrate is provided with an air gap surrounding the heating wire.

14. The micro sensor of claim 1, wherein the substrate is an anodized film obtained by anodizing a metallic base material and removing the base material.

15. The micro sensor of claim 1, wherein at least one of the at least two resistors is a sheet resistor.

16. The micro sensor of claim 1, wherein at least one of the at least two resistors is provided in a pattern shape.

17. The micro sensor of claim 1, wherein at least two of the at least two resistors are connected to each other in parallel.

18. The micro sensor of claim 1, wherein at least two of the at least two resistors are connected to each other in series.

19. The micro sensor of claim 1, wherein the at least two resistors are electrically coupled to each other.

20. The micro sensor of claim 1, wherein the resistor unit further comprises a plurality of resistance pads, and a bottom surface of the sensor electrode is coplanar with bottom surfaces of the at least two resistors and bottom surfaces of the plurality of resistance pads.

* * * * *